United States Patent [19]

Cabanaw et al.

[11] 4,404,419
[45] Sep. 13, 1983

[54] ALKYLATION PROCESS

[75] Inventors: Eldred J. Cabanaw; John W. Mann, both of Bartlesville, Okla.

[73] Assignee: Phillips Petroleum Company, Bartlesville, Okla.

[21] Appl. No.: 408,590

[22] Filed: Aug. 17, 1982

[51] Int. Cl.³ ............................................. C07C 2/58
[52] U.S. Cl. ................................. 585/723; 585/712
[58] Field of Search ............................. 585/723, 712

[56] References Cited

U.S. PATENT DOCUMENTS

| | | | |
|---|---|---|---|
| 2,818,459 | 12/1957 | Gantt | 585/717 |
| 3,647,905 | 3/1972 | Chapman | 585/719 |
| 3,763,022 | 10/1973 | Chapman | 585/723 |
| 3,911,043 | 10/1975 | Anderson | 585/723 |
| 4,144,281 | 3/1979 | Chapman et al. | 585/702 |
| 4,167,535 | 9/1979 | Carson | 585/723 |
| 4,189,616 | 2/1980 | Liebert | 585/701 |

*Primary Examiner*—Curtis R. Davis

[57] ABSTRACT

An alkylation process comprising an isoparaffin feed fractionation zone, an alkylation zone, and an alkylation product fractionation zone wherein a normal paraffin stream separated from the product fractionation zone is charged, preferably after defluorination, to the feed fractionation zone at a locus between interheating and high purity normal paraffin withdrawal, and wherein interheating is effected by use of isoparaffin vapor separated from the product fractionation prior to return to the alkylation zone.

9 Claims, 1 Drawing Figure

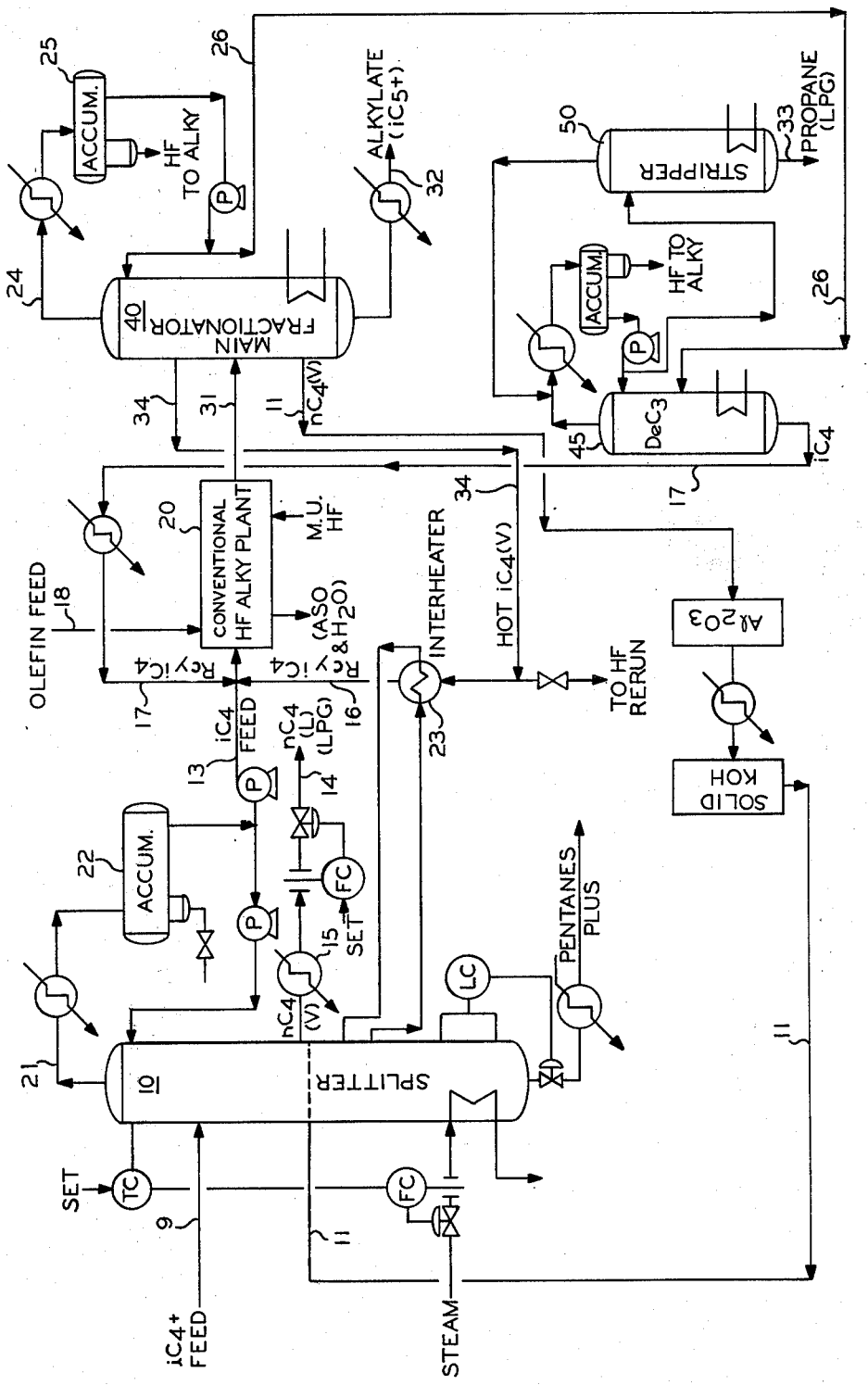

ALKYLATION PROCESS

BACKGROUND OF THE INVENTION

This invention relates to a process for the production of higher boiling hydrocarbons from lower boiling hydrocarbons. In another aspect, this invention is particularly concerned with an improved process for the production of higher molecular weight isoparaffins by the alkylation of lower boiling isoparaffins with olefins in the presence of an acidic alkylation catalyst, such as hydrogen fluoride, in which process maximum utilization is made of available low boiling isoparaffin and with the yielding of high purity normal paraffin. In another aspect, this invention relates to an alkylation process having an isoparaffin containing feed fractionation zone, also known as a butane splitter, an alkylation zone, and an alkylation product fractionation zone, also known as a main fractionation zone or iso-stripper zone.

As is well known, hydrocarbon products can be produced by alkylation reactions involving the combination or condensation of two dissimilar hydrocarbon reactants in the presence of suitable catalytic agents. The alkylation of isoparaffins, such as isobutane, with olefins, such as propylene and/or butylenes, is representative of this type of reaction and has been commonly carried out by feeding isobutane and olefin feedstock in the liquid state, along with the hydrofluoric acid to an alkylation reactor. The reaction product stream can be separated into an acid liquid phase and a hydrocarbon liquid phase, which hydrocarbon phase is then passed to various separation zones in order to recover the various components of the hydrocarbon stream. In some alkylation operations, a feed fractionation zone, called a butane splitter, is installed to upgrade low purity isobutane feed to a higher purity isobutane for use in the alkylation reaction. Also, in the alkylation reaction, a recycle isobutane stream is produced as a vapor side draw from the main fractionation zone. The present invention is directed to an alkylation process having a feed fractionation zone, or butane splitter as it is commonly called, and a main fractionation zone following alkylation and separation of the hydrocarbon phase produced by the alkylation reaction.

Accordingly, an object of this invention is to provide an improved alkylation process.

Another object of this invention is to utilize the available heat in an alkylation plant and the process streams in a more efficient manner.

Another object of this invention is to recover isobutane which is normally lost with the normal butane vapor yielded from the main fractionator.

Another object of this invention is to provide a process of yielding a high purity normal paraffin stream.

It is another object of this invention to cut down on the energy cost of an alkylation process.

Other aspects, objects and the several advantages of the present invention will become apparent to those skilled in the art from a study of the disclosure, drawings, and the appended claims.

SUMMARY OF THE INVENTION

In accordance with the invention, the above objects are achieved by a process comprising an isoparaffin feed fractionation zone, an alkylation zone, and an alkylation product fractionation zone wherein high purity normal paraffin, e.g., normal butane, is recovered from the feed fractionation and isoparaffin, e.g., isobutane, recovered from the product fractionation is used for interheating (indirect heat exchange) the feed fractionation and is then recycled to the alkylation zone.

In a specific embodiment of the invention, normal paraffin vapor, e.g., normal butane vapor, recovered from the product fractionation zone or main fractionator is charged, preferably after defluorination, to the feed fractionation or butanes splitter at a locus between the interheating and the purified normal paraffin, e.g., normal butane, side draw.

In addition to the above specific embodiments, indirect heat exchange interheating of the feed fractionation, or butane splitter, is effected by use of a portion of the hot isoparaffin vapor, e.g., isobutane vapor, separated from the product fractionation of alkylation hydrocarbon products. The isobutane vapor after heat exchange is recycled to the alkylation reaction. The isoparaffin to which this invention is most applicable is that of isobutane.

Further, in accordance with the invention, high purity or LPG grade normal butane is recovered from the feed fractionation zone. This normal butane is recovered in the feed fractionation zone from the isobutane stream charged as feed to the feed fractionation zone, this isobutane stream having normal butane therein, and from the normal butane vapor stream recovered from the main fractionator, this normal butane vapor stream having isobutane there. Normally, this normal butane vapor from the main fractionator is yielded as product; however, this normal butane vapor contains valuable isobutane which is a reactant for the alkylation. By charging this normal butane vapor stream to the feed fractionation zone, high purity normal butane is recovered as product (LPG), and also isobutane is recovered for charge to alkylation.

DETAILED DESCRIPTION OF THE INVENTION

This invention relates to an alkylation process in which energy is used efficiently and effectively and the high purity or LPG grade normal butane stream is recovered as a vapor side draw from the feed fractionator or butane splitter. In addition, a low purity normal butane stream vapor (contains isobutane and isopentane) is produced from the product or main fractionation or isostripper zone, which is preferably subjected to defluorination and caustic treatment to remove trace HF and organic fluorides, and then this stream is charged to the butane splitter, either combined with the primary feed or, preferably, introduced as a secondary feed in the lower section of the feed fractionator. The result is that this low purity normal butane stream is upgraded to LPG quality normal butane by rejecting sufficient isopentane and heavier components (gasoline components) out of the bottom of the feed fractionator, and recovering isobutane overhead from the feed fractionator as additional isobutane feed to alkylation.

The process of this invention comprises the reaction of an isoparaffin of which isobutane is the most preferred and in which context this invention will be described and olefins such as propylene and/or the butylenes in the presence of a catalyst such as hydrofluoric acid in an alkylation reaction zone. The type of reaction zone is not of significant importance and one that is commonly used for this type of reaction is a riser reactor (see U.S. Pat. No. 3,213,157). The conditions obtained in the alkylation reaction zone are conventional temperatures, pressures, contact times, hydrocarbon ratios, and catalyst to hydrocarbon ratios. A typical operation will include a temperature in the range of about 40° F. to about 120° F., pressure sufficient to maintain liquid phases, and isoparaffin olefin volume ratio or about 4:1 to about 20:1 and HF to total hydrocarbon ratio of about 0.5:1 to about 10:1.

The sole FIGURE is a schematic flow diagram illustrating a specific embodiment of the invention as applied to a combination process for production of high octane alkylate, and high purity or LPG grade normal butane, and for sufficient and effective use of energy. The process of the invention will now be described with reference to the drawing.

It is to be understood that numerous items of equipment, such as pumps, valves, and the like, have been omitted from the drawing so as to simplify the description of the invention. Those skilled in the art will realize that such conventional equipment can be employed as desired.

DESCRIPTION OF THE DRAWING

An isoparaffin feed comprising isobutane, normal butane, isopentane and heavier is charged to feed fractionator or butane splitter 10 by way of feed line 9. The isoparaffin feed in line 9 is introduced through an upper portion of splitter 10. Butane splitter 10 is operated under conditions such that a stream rich in isobutane is removed overhead by line 21 and after cooling is passed to accumulator 22. Overhead stream 51 comprises propane, isobutane and normal butane, the predominant component being isobutane.

A bottoms stream 12 comprising normal butane and isopentane and heavier hydrocarbons with trace amounts of isobutane is removed in response to bottoms product level control from splitter 10 for further processing as desired.

A high purity normal butane vapor stream removed as a side draw from splitter 10 by way of lines 14. The point of withdrawal of side stream 14 is below the point of introduction of feed in line 9. Side stream 14 is comprised principally of normal butane with small amounts of isobutane and isopentane plus being present. Stream 14 is condensed in cooler 15. The rate of withdrawal of now liquid side stream 14 can be controlled by way of a flow control means which regulates a flow control valve in line 14.

At a point below side stream 14 withdrawal, a liquid side stream is removed from column 10 and passed through heater 23 for indirect heat exchange with a hot isobutane vapor stream 34 and the heated side stream is returned to column 10 at a point near the point of withdrawal, preferably at a point above its withdrawal, but below the point of withdrawl of vapor side stream 14.

A normal butane containing stream 11 is introduced into column 10 at a point below the point of feed introduction for line 9 and below the point of withdrawal of normal butane vapor by line 14. The normal butane containing stream 11 is withdrawn from the main fractionator following alkylation to be described hereinafter.

Heat to be added into a lower portion of column 10 by way of steam or other heating medium is passed through coils in indirect heat exchange with the reboiler section of column 10. The rate of flow heat exchange medium can be controlled as illustrated in the drawing by means of a temperature controller sensing the temperature of the upper portion of column 10. This temperature set in the top portion of column 10 is to minimize normal butane passing out in conduit 21.

Feed fractionator 10 or butane splitter 10 can be operated under conditions of temperature and pressure such that a stream predominantly comprising isobutane is taken overhead, a stream comprising predominantly normal butane (as vapor) is taken at an intermediate such as withdrawal at an intermediate portion of column 10 and heavier materials (isopentane and heavier) are removed as bottoms. Representative conditions include a top temperature in the range of 115° F. to 130° F. and a bottom temperature of about 175° F. to 190° F. and a pressure in the range of about 75 to 95 psig.

An isobutane stream 13 is removed from accumulator 22 and passed as part of the reactant to alkylation unit 20. Recycle isobutane stream 16 and 17 can be combined with isobutane stream 13 for charging to the alkylation unit together with olefin feed, which is introduced via line 18. The admixture is contacted with an alkylation catalyst to produce alkylate. In alkylation zone 20, the isobutane and olefin feeds are subjected to alkylation conditions for conventional alkylation, and produce an effluent which can be phase separated into a liquid acid phase and a liquid hydrocarbon phase.

The hydrocarbon phase in line 31 comprises HF, propane, isobutane, normal butane and isopentane and heavier (isopentane and heavier called alkylate) and passed to main fractionator 40 wherein light materials including propane and HF and some isobutane, are taken overhead in stream 24. Isobutane vapor is removed by way of line 34 as an intermediate stream. Normal butane vapor stream 11 (contains isobutane and isopentane) is removed at a lower portion and an alkylate stream 32 is removed as bottoms.

Representative conditions of temperature and pressure that can be employed in main fractionator 40 include a top temperature of 150° F. to 175° F. and a bottom temperature of 400° F. to 430° F. with a pressure in the range of 200 to 240 psig.

The overhead stream removed from fractionator 40 in line 24 is cooled and condensed and then passed to accumulator 25 wherein it is separated into liquid hydrocarbon and liquid acid phase with the hydrocarbon phase being returned in part as reflux to an upper portion of column 40 and the remainder passed via conduit 26 to depropanizer 45. Depropanizer 45 is conventional and is operated so as to take overhead propane and HF and a bottoms stream 17 comprising isobutane which is recycled to alkylation unit 20. A portion of the overhead stream from depropanizer 45 is passed to stripper 50 to remove residual amounts of HF and recover product stream 33 as LPG grade propane.

A side stream 11 comprising normal butane is removed from column 40 and passed by way of line 11 through defluorination and neutralization and returned to splitter 10 and introduced at a point below the feed introduced by 9. The defluorination and neutralization steps are conventional.

Side stream 34 comprising isobutane vapor is removed from column 40 and passed through interheater 23 for indirect heat exchange with a side stream from column 10 and then passed by line 16 for recycle to alkylation unit 20.

Normal butane containing stream 11 comprises isobutane, normal butane and isopentane and heavier hydrocarbons, and by operating according to the invention, we recycle this stream to splitter 10 which results in upgrading this low purity normal butane stream 11 by rejecting sufficient isopentane and heavier compounds via 12 out of the bottom of butane splitter 10, recovering normally lost isobutane from stream 11 by way of conduit 21, and recovering a high purity or LPG grade of normal butane from the vapor side draw of the butane splitter in line 14. This vapor is condensed as the LPG normal butane yield.

The operation of a typical system such as shown in the drawings is reflected in the material balance of the following tabulation wherein the materials of the numbered columns represent the materials at the location of corresponding numbers on the drawing.

| I. OPERATING CONDITIONS (Calculated Example) | |
|---|---|
| Splitter (10) | |
| Pressure, psig | 85 |
| Temperature, °F., | |
| Top | 123 |
| Bottom | 182 |
| At Interheat | 156 |
| No. of Trays | 80 |
| HF Alkylation Plant (20) | |
| Conventional | |
| Main Fractionator (40) | |
| Pressure, psig | 220 |
| Temperature, °F. | |
| Top | 163 |
| Bottom | 422 |
| No. of Trays | 74 |
| Depropanizer (45) - Stripper (50) | |
| Conventional | |

| II. FLOWS, BBL/DAY | | | | | | | | | | | | |
|---|---|---|---|---|---|---|---|---|---|---|---|---|
| Stream No. | (9) | (11) | (12) | (13) | (14) | (16)[a] | (17) | (18) | (31) | (32) | (33) | (34)[a] |
| Component (B/D) | | | | | | | | | | | | |
| HF | — | — | — | — | — | 9.5 | — | — | 242.7 | — | — | — |
| Propane | 32.6 | — | — | 32.6 | — | 347.5 | 19.2 | 46.1 | 451.6 | — | 81.3 | — |
| Propylene | — | — | — | — | — | — | — | 17.0 | — | — | — | — |
| Isobutane | 1740.0 | 17.6 | 1.4 | 1696.1 | 60.1 | 23044.9 | 1839.7 | 692.7 | 24916.2 | 1.4 | 1.2 | — |
| Normal Butane | 1157.0 | 312.5 | 303.8 | 56.6 | 1109.1 | 1729.1 | 95.3 | 323.2 | 2204.6 | 69.9 | — | — |
| Butylenes | — | — | — | — | — | — | — | 2045.4 | — | — | — | — |
| Isopentane plus | 373.4 | 94.0 | 445.0 | — | 22.4 | 446.9 | 0.3 | 82.1 | 4205.0 | 3805.1[b] | — | — |
| Total B/D | 3,303.0 | 424.1 | 750.2 | 1785.3 | 1191.6 | 25577.9 | 1954.5 | 3206.5 | 32020.1 | 3876.4 | 82.5 | — |

[a] Streams 16 and 34 are substantially the same. Small amount of 34 goes to HF rerun (not shown).
[b] (32) is alkylate gasoline.
NOTE:
Stream 11, conventionally yielded, is 73.7 volume percent normal butane.
Stream 14, of our invention, is 93.1 volume percent normal butane.

We claim:

1. In an alkylation process which comprises the steps of:
   (a) subjecting an isoparaffin-containing feed comprising isoparaffins and normal paraffins to fractionation under conditions to separate same into an overhead stream enriched in isoparaffins, an intermediate side stream of high purity normal paraffins, and a bottoms stream comprising higher boiling isoparaffins and normal paraffins,
   (b) passing said overhead stream enriched in isoparaffins to an alkylation zone and therein contacting same with an olefin and an alkylation catalyst under alkylation conditions to form an alkylation effluent and recovering from said effluent a hydrocarbon phase comprising alkylate, isoparaffins and normal paraffins,
   (c) passing said hydrocarbon phase to a second fractionation operated under conditions to separately recover an isoparaffin vapor stream, a normal paraffin vapor stream, and an alkylate product stream; and
   (d) passing said normal paraffin vapor stream to said fractionation in (a) at a locus below the point of withdrawal of said side stream of high purity normal paraffins.

2. A process according to claim 1 wherein a second intermediate side stream is withdrawn from said fractionation in (a) at a locus below the point of withdrawal of said high purity normal paraffins and subjected to indirect heat exchange and returned to said fractionation at a point above the point of removal of said side stream but below the point of removal of said normal paraffin stream.

3. A process according to claim 2 wherein at least a portion of said indirect heat exchange is effected by use of a portion of said isoparaffin vapor stream separated in (c).

4. A process according to claim 2 wherein said normal paraffin stream separated in (d) is charged to said fractionation in (a) at a locus below the point of removal of said normal paraffin stream and a point above the reintroduction of said side stream to said fractionation.

5. A process according to claim 3 wherein said isoparaffin vapor stream is recycled to the alkylation reaction zone after said indirect heat exchange with said side stream.

6. A process according to claim 1 wherein said normal paraffin stream separated in (c) is subjected to defluorination prior to charging to said fractionation in (a).

7. A process according to claim 1 wherein said isoparaffin-containing feed in (a) comprises isobutane, normal butane, propane and pentanes and heavier hydrocarbons, and wherein said alkylation catalyst is HF acid.

8. A process according to claim 1 wherein a side stream is withdrawn from said fractionation in (a) at a locus below the point of withdrawal of said high purity normal paraffin and subjected to indirect heat exchange and returned to said fractionation in (a), and wherein at least a portion of said indirect heat exchange is effected by use of a portion of said isoparaffin vapor stream separated in (c), and further wherein said isoparaffin vapor stream is recycled to the alkylation reaction zone after said indirect heat exchange with said side stream.

9. A process according to claim 8 wherein said normal paraffin stream separated in (d) and charged to said fractionation in (a) at a locus between the point of removal of said normal paraffin stream and the point of reintroduction of said side stream to said fractionation, and wherein said isoparaffin-containing stream feed in (a) comprises isobutane, normal butane, propane, and $C_5$ and heavier hydrocarbons, and wherein said alkylation catalyst is HF acid.

* * * * *